Figure 1:
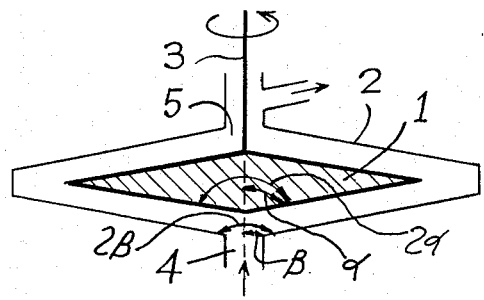

United States Patent [19]
Kepes

[11] 4,334,424
[45] Jun. 15, 1982

[54] PROCESS FOR DETERMINING THE RHEOMETRIC PROPERTIES OF MATERIALS AND APPARATUS CARRYING OUT SAID PROCESS

[76] Inventor: André Kepes, 22 Av. de la Prise d'Eau, Le Vesinet, France, 78110

[21] Appl. No.: 122,473

[22] Filed: Feb. 19, 1980

[30] Foreign Application Priority Data

Feb. 22, 1979 [FR] France .................. 79 04585

[51] Int. Cl.³ .................................. G01N 11/14
[52] U.S. Cl. .................................. 73/59
[58] Field of Search .................................. 73/59, 60

[56] References Cited

U.S. PATENT DOCUMENTS 2,305,531 12/1942 Hurndall .................. 73/60
3,387,490 6/1968 Wise .................. 73/60

FOREIGN PATENT DOCUMENTS 45-27871 11/1970 Japan .................. 73/59
200310 12/1967 U.S.S.R. .................. 73/60
450992 5/1975 U.S.S.R. .................. 73/59

Primary Examiner—Anthony V. Ciarlante
Attorney, Agent, or Firm—James E. Nilles

[57] ABSTRACT

The present invention relates to a process for determining the rheological properties of fluid, consisting in completely filling a space located between a body constituted by a double cone of vertex angle $2\alpha,\alpha$ being smaller than 90° and a biconical surface, of the same axis as the axis of said double cone, of vertex angle $2\beta,\beta$ being equal to or smaller than 90°, then said material is subjected to strains by driving said double cone or said biconical surface around the common axis. The non-driven element remaining fixed, said drive being effected with the aid of a device by which either a speed or a torque is imposed, according to a known program, on the driven element, and the parameter—speed or torque—which is not imposed is measured. The invention also relates to an apparatus for carrying out said process.

3 Claims, 5 Drawing Figures

PROCESS FOR DETERMINING THE RHEOMETRIC PROPERTIES OF MATERIALS AND APPARATUS CARRYING OUT SAID PROCESS

The present invention relates to a process for determining the rheometric properties of materials and to apparatus for carrying out this process.

The industrial importance of measuring the rheological properties of materials is known; the principle of these measurements consists in subjecting a material, which is in a determined state, to a certain number of known and monitored strains (for example shearing) and in measuring the reaction of said material to these strains.

A certain number of apparatus are also known, designed for determining the rheological properties of materials. For example, for measuring the viscosity of fluid materials, devices of the rheogoniometer type or devices of the grader type have already been recommended. In the devices of the rheogoniometer type, the fluid of which it is desired to measure the rheological properties, for example the viscosity, is introduced between two surfaces, one of which is plane and the other is either plane and parallel to the first, or in the form of a cone whose axis is perpendicular to the plane of the first surface; one of the surfaces is subjected to a monitored rotary movement and the reaction exerted by the fluid subjected to the described stresses on the second surface is determined by known means; the major drawback of the devices of the rheogoniometer type lies in the indetermination introduced by the existence of the lateral "edges" of the fluid volumes. In the devices of the grader type, the fluid to be studied is introduced into a tube and the flow of said fluid in said tube is measured under determined experimental conditions. The major drawbacks of the devices of this type lie in the necessarily discontinuous character of the measurement, in the impossibility of using it for servo-control and in very poor precision.

It is an object of the present invention to propose a process for determining the rheological properties (particularly the visco-elasticity and viscosity) of a fluid material, and an apparatus for carrying out this process.

The process is characterized by the steps of admitting the material, under determined physical conditions and with a known rate of flow, to completely fill a space located between a body constituted by a double cone of vertex angle $2\alpha$, $\alpha$ preferably being smaller than 90°, and a biconical surface, on the same axis as the axis of said double cone, of vertex angle $2\beta$, $\beta$ being equal to or smaller than 90°, then subjecting said material to strains by driving said double cone or said biconical surface around the common axis, the non-driven element remaining fixed, said drive being effected with the aid of a device by which either a speed or a torque is imposed, according to a known programme, on the driven element, and measuring the parameter—speed or torque—which is not imposed.

It is indispensable, for the process to allow valid, reproducible measurements of the rheological properties of material, to be able to control and/or know the operational conditions. For example, one must be sure that the material completely fills all the space in which it must be admitted, without the possibility of making air bubbles. This essential condition implies that certain precautions are taken when filling the apparatus. All the physical parameters (particularly the temperature) of the material must also be known perfectly. However, in addition, the circulation (rate of flow) conditions of the material in the space that it fills must be known, even though this flow may possibly be zero (measurement in the stationary state).

The drive of one of the elements (double cone or biconical surface) must be effected according to well determined systems. Thus, this drive may consist in the production of a rotation in a determined direction, and controlling the speed of rotation or the torque. However, the drive may be effected according to other systems such as, for example, an alternative system in which the element is subjected to different, determined and programmed efforts which drive it in rotation in one direction or in different directions. This alternative system may, for reasons of mathematical interpretation of the results, be of sinusoidal nature.

The present invention also relates to an apparatus for carrying out the described process.

The rheometer according to the invention is characterized in that it comprises:

a body constituted by a double cone of vertex angle $2\alpha$, $\alpha$ preferably being smaller than 90°;

a cavity which may contain said double cone, the cavity itself presenting a biconical inner surface of vertex angle $2\beta$, $\beta$ being equal to or smaller than 90°;

means enabling said body to be placed in said cavity so that the axes of the double cone and of the biconical inner surface of the cavity merge;

means for driving said double cone or said cavity in rotation about the common axis, the non-driven element remaining fixed, said drive being effected with the aid of a device in which either the speed or the torque is imposed;

means for measuring the parameter—speed or torque—which is not imposed;

means for conducting the fluid to be studied between said body and the inner surface of the cavity, these means ensuring that the space between said body and said surface is filled with said fluid and enabling the conditions of circulation (rate of flow) of said fluid through said space to be known, the inlet and outlet of the fluid being effected via pipes located along the axis of the cones, and means for monitoring the physical parameters determining the state of the fluid.

In the rheometer according to the invention, a drive with imposed torque and a measurement of the speed of rotation are preferably used, this being necessary when the rheometer is used as a "grader".

The inlet of the fluid in the air gap, i.e. between the body and the inner surface of the cavity, is effected through an axial channel formed in the element—body or cavity—remaining fixed. The fluid passes through the whole of the air gap (and is subjected to shear during this passage) in a divergent, then convergent flow. The fluid is evacuated in a region located on the side of the apparatus, either on the driving shaft side when the cavity is fixed or on the side opposite the driving shaft when the body is fixed.

Schematic diagrams of the rheometer-grader according to the invention are shown in FIGS. 1 to 5.

The body is constituted by two cones connected by their base thus forming a double cone. The two cones forming the double cone are generally identical, although this condition is not imperative. A cross section of this double cone presents two vertex angles 2α, α preferably being smaller than 90°; in general, α is fairly large, preferably more than 60°. This body is made of metal, for example stainless steel.

The body is positioned in a cavity presenting a biconical inner surface. There again, the general form of said surface is that of two cones joined symmetrically by their base. A cross section of the cavity is such that the cones have two vertex angles 2β, β being equal to or smaller than 90°; when β is equal to 90°, the cavity is generally in the form of a portion of cylinder; when β is equal to α, the opposite surfaces of the body and the cavity are parallel; β may be different from α, either larger or smaller; β is preferably larger than α and the vertices of the opposite cones merge; in general, β is fairly large, preferably more than 60°. The cavity is in a piece made of a metal, for example stainless steel.

The body is preferably disposed in the cavity so that the axes of the double cone forming said body and of the biconical surfaces forming the cavity are merged or aligned; when the cavity is in the form of a cylinder (β=90°), the axis of the double cone is merged or aligned with the axis of the cylinder.

The body placed in the cavity determines or defines in this cavity a space, or air gap, which is the space located between the surface of the body and the inner surface of the cavity.

The body (or the piece forming the cavity) is provided with means for rotating it about its axis, it being understood that the other piece remains fixed. This drive is preferably effected with the aid of a device with imposed torque; in fact, said torque obviously remains imposed during a measurement or part thereof, but the value of the torque may be modified as desired from one measurement to another or in the course of a measurement. The torque applied to the body or to the cavity, being given the speed of rotation acquired by the mobile element, will depend on the rheological properties of the fluid present in the air gap and may constitute a measurement or marking of the viscosity of said fluid; a means for measuring this speed of rotation will therefore furnish information on the viscosity of the fluid.

The apparatus according to the invention will be completed by means allowing the inlet of the fluid in the air gap under determined conditions (particularly temperature) and also the maintaining of constant operational conditions for the whole duration of the measurement when measurement is effected under stationary conditions; the apparatus will also comprise means for evacuating the fluid.

The invention will be more readily understood on reading the following description with reference to the accompanying drawings, in which the Figures show various embodiments of the invention in section.

Figure 2:
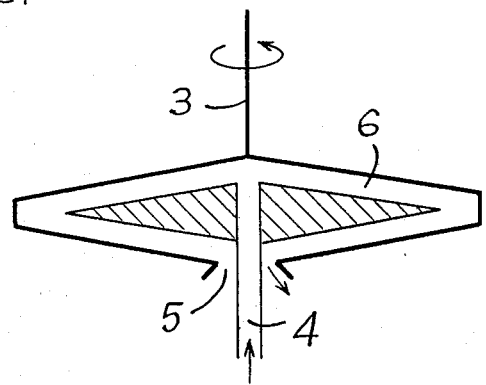
Figure 3:
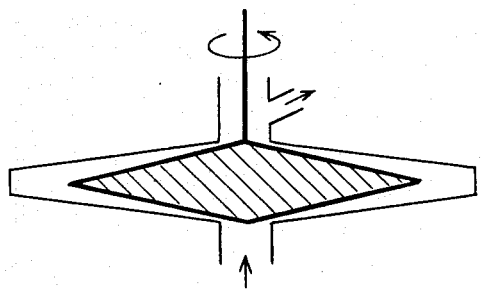
Figure 4:
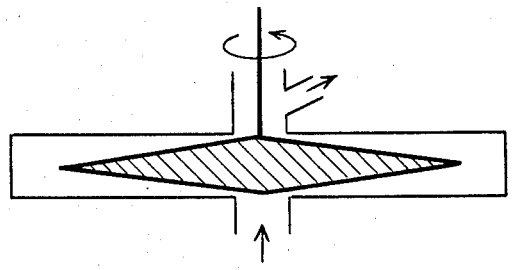

FIG. 1 shows at 1 the body, at 2 the fixed piece comprising the cavity, at 3 the shaft enabling the body 1 to be rotated due to the application on said shaft of a constant torque, at 4 a tube for the inlet of the liquid to be studied, at 5 a device for the outlet of the liquid; in this embodiment, it will be noted that the opposite surfaces of the body and of the cavity are parallel and that it is the body which is rotated;

In FIG. 2, the same elements as in FIG. 1 are found; however, the inlet of the liquid to be studied is effected through a tube 4 which conducts said liquid, along the axis of the body, into the air gap 6; the liquid leaves at 5; moreover, the body is fixed and it is the piece comprising the cavity which is driven in rotation at constant torque by the shaft 3; in this embodiment, the opposite surfaces of the body and of the cavity are parallel;

FIGS. 3 and 4 simply show two schematic embodiments of the body-cavity assembly; in FIG. 3, the opposite surfaces of the body and the cavity progressively diverge from each other on moving away from the axis, as the angle α is smaller than angle β; in FIG. 4, the surface of the cavity has the form of a cylinder of circular section; in this case, the angle β is equal to 90°; moreover, the vertices of the cones of the body and the cavity are merged.

Figure 5:
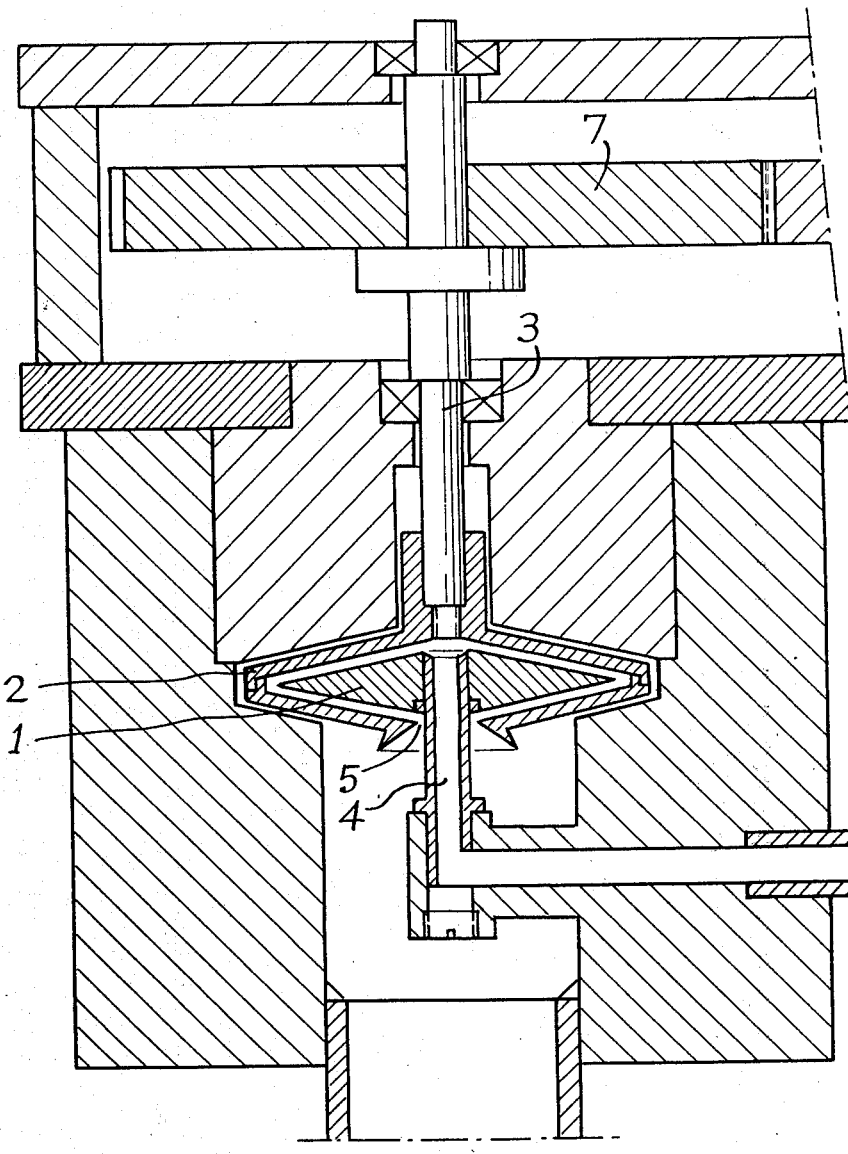

FIG. 5 shows, in section, a diagram of the essential parts of an apparatus according to the invention.

The body 1 is placed in the cavity of a piece 2; this piece 2 is formed by two parts screwed to each other so as to form the cavity in which the body 1 has been introduced. The piece 2 is fixed on a shaft 3 which is driven by a D.C. motor (not shown) via a gear down mechanism 7; the fluid is admitted through the pipe 4 which passes through the body along its axis; the body is fixed; in the embodiment shown, the opposite surfaces of the body and the cavity are parallel; the fluid leaves through the opening 5 made around the pipe 4.

The functioning of the rheometer-grader according to the invention may be described as follows:

(1) when α=β and for α close to 90°, the fluid is subjected to a "torsional flow" similar to the one to which it is subjected between two parallel discs. The speed gradient to which an elementary volume of fluid is subjected increases linearly with its distance to the axis where it is zero.

If a drive torque is imposed such that the maximum tension at the edge of the double cone is identical to that which the standards in force impose at the level of the walls of the capillary tube of a grader, the apparatus may directly furnish a measurement (speed of rotation) very close to the melting index of the polymer used as fluid, as it is subjected to a system of strains of the same value and the same spatial distribution.

(2) When α is different from β and the vertices of the conical surfaces coincide in two's, a flow of constant gradient is effected; the rheometer then furnishes other information on the rheological properties of the fluid studied.

The fluid may be studied by stationary, transitory or alternative systems; with a stationary system, the fluid, once introduced into the air gap, stops there until the speed of rotation reaches its equilibrium; with a transitory system, the fluid circulates through the air gap with a given rate of flow and the speed of rotation obtained is studied; with alternative systems (generally usable during a stop in the circulation of the fluid), the shaft ensuring the rotation (of the body or of the cavity) is subjected to torques which vary in time according to known laws.

The advantages of the device according to the invention are numerous and the following may be mentioned for example:

(a) elimination of the necessity of the guard ring; it is known that, in rheometric devices of the cone and plane type, the measurements are rendered delicate by the effects of edges which often require the use of a guard ring; in the apparatus according to the invention, there is no guard ring; there is therefore no undue stagnation of the fluid and dirtying of the ring; the tested fluid may therefore be heterogeneous (suspension, emulsion, etc.) or even abrasive;

(b) balancing of the forces at each point of the device, particularly of the normal forces developed by the shear of the polymers, and the centrifugal forces exerted on the fluid;

(c) relatively slight errors resulting from decentring or mechanical clearances of the moving pieces;

(d) possibility of continuous feed by a viscous (molten) product, such as a polymer which may be under pressure, and also possibility of feed programmed in time.

It is possible, for the person skilled in the art, without departing from the scope of the invention, to use all known technical means for materially carrying out the invention.

Thus, for example, the drive motor with determined torque will preferably be a D.C. motor with an iron-less armature; this motor may advantageously be capable of furnishing a torque proportional to the feed current; for measuring the grade of a product, said torque will be imposed and will correspond to the tension standardised for the studied product at the edge of the double cone, but, for the study version, said torque will be chosen by the experimenter and may if necessary be servo-controlled; however, it would be possible to use any other means for obtaining an imposed torque. Thus, the simplest means for measuring the drive speed—this speed being a function of the viscous or elastic properties of the fluid in the air gap—consists in taking the electrical voltage at the terminals of a tachometric winding, but it will be possible to use any known means for marking and/or measuring said speed.

In an embodiment of the invention, a body has been used whose symmetrical double cone had an angle $\alpha$ of 80°; this double cone was disposed in a cavity whose inner surface was also biconical and symmetrical and having an angle $\beta$ of 80°; the air gap was therefore constituted by parallel surfaces; the diameter of the base of the double cone constituting the body was 40 mm; the air gap was 2 mm. Under these conditions, the properties of a grade 1 polyethylene were measured under normal temperature conditions; for a torque of 4992 g/cm on the shaft, a speed of rotation of 2.37 rpm was obtained; if a grade 25 polyethylene is used, this same torque leads to obtaining a speed of rotation of 59.25 rpm.

What is claimed is:

1. Apparatus for determining the rheological properties of a fluid material comprising:
   a first component having a cavity therein;
   a second component mounted within said cavity, said second component being biconical in shape;
   said first and second components being relatively rotatable with respect to each other;
   means for effecting rotation of said first component relative to the other;
   and conduit means for introducing and removing said fluid material from said cavity, said conduit means including an inlet passage extending through the bottom of said cavity and through the second component, said conduit means including an outlet passage disposed at the bottom of said cavity around and separated from said inlet passage.

2. Apparatus according to claim 1 wherein said cavity is biconical in shape.

3. Apparatus according to claim 2 wherein said second component has surfaces parallel to surfaces of said cavity.

* * * * *